United States Patent [19]

DuRoss

[11] Patent Number: 5,178,850
[45] Date of Patent: Jan. 12, 1993

[54] CRYSTALLINE SUGAR ALCOHOL CONTAINING UNIFORMLY DISPERSED LIQUID PHARMACEUTICAL COMPOUND

[75] Inventor: James W. DuRoss, Smyrna, Del.

[73] Assignee: ICI Americas Inc., Wilmington, Del.

[21] Appl. No.: 538,966

[22] Filed: Jun. 15, 1990

Related U.S. Application Data

[63] Continuation-in-part of Ser. No. 213,863, Jun. 30, 1988, abandoned.

[51] Int. Cl.⁵ .......................... A61K 9/68; A61K 7/16; A61K 47/00; A61K 9/28
[52] U.S. Cl. ........................................ 424/48; 424/49; 424/439; 424/440; 424/441
[58] Field of Search ................... 424/48, 49, 439, 440, 424/441

[56] References Cited

U.S. PATENT DOCUMENTS

| | | | |
|---|---|---|---|
| 3,200,039 | 8/1965 | Thompson, Jr. | 424/469 |
| 3,935,326 | 1/1976 | Groppenbacher et al. | 427/3 |
| 4,252,794 | 2/1981 | DuRoss | 514/777 |
| 4,260,596 | 4/1981 | Mackles | 424/440 |
| 4,610,871 | 9/1986 | Lynch | 424/48 |

OTHER PUBLICATIONS

Appln. No. 07/213,863, filed Nov. 22, 1989.

*Primary Examiner*—Nathan M. Nutter
*Attorney, Agent, or Firm*—W. E. Dickheiser; P. L. Sharer

[57] ABSTRACT

A pharmaceutical composition comprising a crystalline sugar alcohol derived from at least one mono- or polysaccharide having at least one liquid pharmaceutically active compound uniformly dispersed within its crystal matrix is disclosed. Also disclosed is a method of producing such a uniformly dispersed pharmaceutical composition by the controlled crystallization of the molten sugar alcohol having the pharmaceutically active material dispersed therein.

8 Claims, No Drawings

CRYSTALLINE SUGAR ALCOHOL CONTAINING UNIFORMLY DISPERSED LIQUID PHARMACEUTICAL COMPOUND

This Application is a continuation-in-part of U.S. patent application Ser. No. 213,863 filed Jun. 30, 1988 and now abandoned.

FIELD OF THE INVENTION

This invention relates to a pharmaceutical composition comprising crystalline sugar alcohol derived from at least one mono- or polysaccharide having at least one liquid pharmaceutically active compound uniformly dispersed within its crystal matrix as well as to a method of producing such a uniformly dispersed pharmaceutical composition.

BACKGROUND OF THE INVENTION

Many active pharmaceutical compounds may only be beneficially employed within very specific dosage ranges, with ineffective or even deleterious effects being encountered if too high or too low a dosage is employed. Accordingly, it is necessary that such compounds be formulated in a uniform manner such that a consistent dosage of such active compound can be readily manufactured and administered.

Particular problems exist with respect to the formulation of actives which are in the form of liquids. One method typically employed involves blending liquid actives with excipients employing wet granulation techniques wherein such ingredients are utilized in the form of a wet paste. The paste is blended with the pharmaceutically active liquid, and the mixture then dried, ground and tableted. However, such wet granulation processes are disfavored by the pharmaceutical industry because they are labor intensive, require special equipment and are highly susceptible to contamination.

Another, more economical, approach which may be employed is to first absorb the liquid active onto an absorbent material and then dry blend the absorbent/active material with powdered excipient and directly form tablets therefrom. However, because of the low levels of the absorbent/active material incorporated and the fine particle size thereof uniform blending is exceptionally difficult, and separation of the absorbent/active material from the excipient mass can occur during the granulation, blending and/or tableting process with the result that the manufactured products do not meet uniform assay requirements.

A third approach which may be employed to minimize the segregation problem, involves encapsulating such actives in gelatin or other film formers. However, such encapsulation may not effectively prevent segregation as in many instances separation may occur upon the grinding or milling of such encapsulates. Moreover, such a process increases the number of formulating steps required and thus involve the incurring of additional expense.

Thus, it would be desirable to possess a pharmaceutical composition which contains a uniform concentration of liquid active material, which composition can be easily and inexpensively manufactured with low risk of contamination.

Accordingly, it is an object of this invention to provide a pharmaceutical composition having a uniform dispersion of liquid active material.

It is a further object of this invention to provide a process for economically preparing a pharmaceutical composition having a uniform dispersion of liquid active material.

The above objects and other additional objects will become more fully apparent from the following description and accompanying Examples.

SUMMARY OF THE INVENTION

In one aspect, the present invention is directed to a pharmaceutical composition comprising at least one crystalline sugar alcohol derived from a mono- or polysaccharide having at least one liquid pharamceutically active compound uniformly dispersed within its crystal matrix.

In another aspect, this invention is directed to a process for producing a pharmaceutical composition having uniformly dispersed liquid pharmaceutically active compound therein comprising the steps of:
(A) forming a molten sugar alcohol derived from at least one mono- or polysaccharide;
(B) dispersing at least one liquid pharmaceutically active material in said molten sugar alcohol under conditions such that a homogeneous mixture is formed;
(C) cooling said homogeneous molten mixture under agitation until a viscous mass is formed; and
(D) cooling said mass slowly until the sugar alcohol becomes fully crystallized.

DESCRIPTION OF THE PREFERRED EMBODIMENTS

The pharmaceutical compositions of this invention are comprised of at least one crystalline sugar alcohol derived from a mono- or polysaccharide having at least one liquid pharmaceutically active compound uniformly dispersed within its crystal matrix.

The sugar alcohols which may be employed in the practice of this invention are well known to those of skill in the art and are typically produced by the catalytic hydrogenation of mono- and/or polysaccharides derived from carbohydrates which are high molecular weight polymers derived from pentose and hexose units. Illustrative of such saccharide materials are sugars, such as dextrose and maltose; cellulose; starch; and wood sugars. These materials are typically hydrolyzed under aqueous conditions utilizing enzymes or mineral acids to form monoses, dioses and trioses, etc., which are then catalytically reduced with hydrogen by well known methods. The aqueous solutions of these sugar alcohols formed thereby are then typically treated with ion exchange resins, activated carbon, or the like to form clear solutions.

Illustrative of the sugar alcohols which may be employed in the practice of this invention are mannitol, sorbitol, maltitol, cellobiitol, lactitol, xylitol or a blend of polyols known in the art as hydrogenated starch hydrolysates. The preferred sugar alcohols are sorbitol, and blends of sorbitol with mannitol. When blends of these alcohols are employed, preferably between about 5 and about 15 weight percent mannitol and between about 85 and about 95 weight percent sorbitol are present.

The sugar alcohols employed herein generally are dried such that they have a water content of less than about 3 percent by weight. Preferably such water content is less than about 1 percent, and most preferably is less than about 0.5 percent by weight. The sugar alcohol starting materials may be dried to the desired water content by conventional means such as a continuous thin film evaporator or a batch vacuum cooker.

As is employed herein the term "liquid pharmaceutically active compound" refers to an organic or inorganic orally ingestable compound which is taken for medicinal, dietary and/or nutritional purposes, and which is liquid in form. It is to be noted that this term is intended to cover actives which are normally solid at ambient conditions but which are dissolved in a suitable solvent to regulate the dosage, rate of release, etc. as well as to cover actives which are themselves liquids at ambient temperatures. Illustrative of the pharmaceutically active compounds which may be beneficially formulated by the practice of this invention and which are themselves liquids are alkyl ethers of dianhydrohexitols such as dimethylisosorbide and the like. Illustrative of actives which are normally solids but are formulated in solvent form are compositions such as cimetidine in ethanol, sodium fluoride in water, and the like.

The pharmaceutically active compounds employed in the practice of this invention are liquid in form—i.e., they have a definite volume and will assume the shape of their container at ambient temperatures.

Depending upon the nature of the pharmaceutically active compound employed and upon the means by which the active is added to the molten sugar alcohol, it is possible to uniformly formulate up to about 30 percent or more by weight of pharmaceutically active compound in the sugar alcohol excipient following the process of this invention.

The pharmaceutical composition of this invention is prepared by:

(A) forming a molten sugar alcohol derived from at least one mono- or polysaccharide;
(B) dispersing liquid pharmaceutically active material in said molten sugar alcohol under conditions such that a homogeneous mixture is formed;
(C) cooling said homogeneous molten mixture under agitation until a viscous mass is formed; and
(D) cooling said mass slowly until the sugar alcohol becomes fully crystallized.

In step (A), one of ordinary skill in the art can easily determine suitable operating temperatures by routine experimentation. Typical operating temperature ranges for the following exemplary sugar alcohols are as follows: sorbitol, between about 86° and about 130° C.; mannitol, between about 80° and about 120° C.; xylitol, between about 140° and about 190° C.; maltitol, between about 100° and about 150° C.; lactitol, between about 100° and about 200° C.; cellobiitol, between about 100° and about 175° C.; and hydrogenated starch hydrolysate between about 150° and about 200° C. It should be noted, however, that the deactivation temperature of any particular pharmaceutically active compound must be taken into account when selecting the appropriate sugar alcohol to be employed, as well as the specific temperature within the acceptable operating temperature range for a given sugar alcohol.

In step (B) of the process hereof the pharmaceutically active liquid is dispersed in the molten sugar alcohol under conditions such that a homogeneous mixture is formed. The liquid pharmaceutically active material may either be added directly to the molten sugar alcohol, or such active may first be absorbed into a pharmaceutically acceptable absorbent such as silica gel or biocellulose. As is employed herein the term "pharmaceutically acceptable absorbent" refers to materials capable of absorbing the liquid pharamceutically active material and which exhibit no harmful effects when ingested by humans.

Should step (B) involve the dispersion of pharmaceutically active liquids which have been absorbed into a solid absorbent any one of several techniques may be employed. For example, the molten polyhydric alcohol may be contained in a heated kettle equipped with a high shear mixing device used to create a vortex in the molten material. The active absorbent ingredient may be added gradually to the vortex and agitation continued until such active absorbent material is uniformly dispersed throughout the molten alcohol. In other instances, it may be preferred in certain instances to dry-mix a portion of the finely divided sugar alcohol with the active absorbent material in a ball mill or V-blender to create a uniform blend which is then added to the molten material.

Should it be desired that the liquid pharmaceutically active material be added directly to the molten alcohol then any conventional addition technique may be employed. Care must be taken, however, to ensure that agitation continues at the elevated temperature of the molten alcohol until thorough dispersion of the active compound in the molten sugar alcohol has occured.

Once the pharmaceutically active compound has been uniformly dispersed in the molten alcohol (which point can be readily determined by routine assay for any particular additive/molten alcohol combination), the temperature is reduced while agitation continues. Such cooling with agitation results in the onset of crystallization. Agitation should be continued until the formulation becomes a viscous mass. By the term "viscous mass" is meant a composition which has a semi-solid, dough-like appearance; is extrudable; and is not liquid and runny. Typically, at this point the sugar alcohol is generally at least about 40 percent crystalline by weight. However, where high loadings of active material are present, a viscous mass may be present where as little as only 20 weight percent of the sugar alcohol has crystallized. If desired, the dispersion may be periodically monitored, e.g., by differential scanning calorimetry, until the required percentage crystallinity for a given sugar alcohol/pharmaceutically active compound mixture (which percentage can easily be determined by running trials at various times until a suitable viscous mass is formed and then determining the crystallinity of such viscous mass, e.g. by differential scanning calorimetry) is observed.

The viscous mass is removed from the agitating means and allowed to further cool until a solid crystalline mass having a uniform dispersion of pharmaceutically active composition is obtained. While the mixture can fully crystallize under agitation, this is generally not preferred as such solid material may block up the reactor and even damage the agitation means employed.

The fully crystalline mass may be ground, employing conventional grinding equipment, to provide a powder which can be formed into tablets or blended with additional excipients and formulated into chewing gums, tablets, and the like.

Large scale preparations may preferably be made employing a process wherein the sugar alcohol, preferably sorbitol or a blend of sorbitol and mannitol, is heated to a temperature of between about 80° C. and about 100° C. and subjected to agitation in a heated tank. After addition of the pharmaceutically active compound, under continuous agitation, the reaction mass is then metered into a continuous twin shaft mixer of the intermeshing type. Mixers of this type are discussed in "Chemical Engineers Handbook", 5th Edition, edited by R. H. Perry and C. H. Chilton (1973) pages 19-21. Characteristics of these mixers are that they include intermeshing kneader blades mounted on two parallel shafts which rotate in the same direction at the same speed with close blade-to-wall and blade-to-blade clearances.

A preferred continuous mixer is the high shear Readco Continuous Processor made by Teledyne Readco of York, Pa. The mixer shown U.S. Pat. No. 3,419,250 and in U.S. Pat. No. 3,618,902 (both assigned to Teledyne Inc.) can be used without modification; however, the sugar alcohol magma which is formed in the present process is much more easily handled if the mixer is equipped with an extrusion nozzle or plate. Other high shear continuous twin screw mixers which impart a high shearing force at low shaft speed to the material being processed can also be used. Such mixers include the Baker, Perkins Multi-Purpose (M-P) mixer made by Baker, Perkins Inc. of Saginaw, Mich., and the ZSK Twin Screw Compounding Extruder made by Werner and Pfleiderer Corporation of Stuttgart, Germany. The Baker, Perkins mixer is shown in U.S. Pat. Nos. 3,195,868 and 3,198,491. Alternative blade configurations can be used in mixers of this type are shown in U.S. Pat. Nos. 3,423,074 (assigned to Baker, Perkins) and 3,490,750 (assigned to Teledyne, Inc.). These mixers are available in various diameters and horse power ratings depending on the throughput required.

Preferably, a Readco Continuous Processor with kneader blade diameters of 5, 15 or 24 inches with feed and/or discharge screws is utilized. Further, the discharge nozzles are preferably provided with heating means in order that the surface of the partially solidified cylindrical ribbon of exiting magma does not prematurely crystallize ensuring a smooth discharge. Thus, one process for producing the pharmaceutical compositions of this invention involves continuously introducing a feed comprising the molten magma containing the added pharmaceutically active compound into an elongated mixing zone having shaft means and a plurality of kneader blades mounted on the shaft means, the configuration of the kneader blades being such as to provide restricted clearances between the blades and the adjacent walls; simultaneous cooling and kneading the molten alcohol magma as it passes through the mixing zone until a viscous mass of molten sugar alcohol and active is obtained; and continuously discharging the blend from the mixing zone through an extrusion orifice and further cooling the blend to ambient temperature forming the crystalline sugar alcohol containing included active material.

In carrying out the crystallization, the molten sugar alcohol is preferably held in an agitated feed tank in a relatively dry atmosphere to inhibit moisture pickup such that the moisture content does not exceed about 1% by weight. This precaution becomes less of a factor as the temperature of the molten alcohol mix exceeds 100° C. At this point, the active material, either in liquid form or absorbed into a pharmaceutically acceptable absorbent, is added under agitation (e.g., high shear mixing) blended with some of the crystalline polyol, or with melted polyol or melted and/or dispersed in molten polyol, depending on the melt temperature of the polyol as well as on the specific physical characteristics of such active material. In the operation of the mixing equipment, the feed rate and other operating parameters are adjusted such that as the cooling mass passes through the mixer, a molten blend having increased concentrations of crystals is generated as the magma passes through from the feed to the discharge orifice. The rotating screws move the molten magma containing crystals and dispersed active from the center of the equipment to the outer cooled edge whereupon additional crystals are precipitated and remixed with additional molten alcohol and active to act as a crystallizing seed. As the temperature profile drops from molten feed temperature to discharge temperature, the viscosity of melt increases due to the formation of the crystals. The action of the rotating screws pushes the crystallizing molten magma containing dispersed ingredient in the form of extrudate through the discharge orifice whereupon it is extruded as an elongated mass. The extrudate may then be conveniently cut into desired lengths and permitted to cool until crystallization is complete.

Care should be taken to ensure that the temperature of the emitted extrudate is not too hot, as the molten mass will lose its shape. Not only is such material difficult to handle, but the product obtained may be an undesirable mixture of crystals and amorphous sugar alcohol glass, having a nonuniform dispersion of the active material therein. The problem can be corrected by decreasing the throughput time or jacket cooling temperature and other variables such as feed temperature, rotation speed, back pressure, etc. Under ideal operating conditions, the extrudate crystalline paste develops a solid outer shell of crystalline product which is only slightly wetter on the interior side with molten material. The hot extrudate when permitted to stand will fully crystallize, typically over a period of between about 6 hours or less and about 96 hours or more depending on the cross-sectional dimension of the extrudate mass (which typically ranges in cross-section from about 5 to about 20 millimeters) and the effect of the added ingredient. Longer periods may be required for extruded shapes having a cross-sectional dimension of greater than 20 millimeters.

The extrudate may subsequently be formulated into various end uses such as tablets, chewing gum, toothpaste and the like using methods and formulations well known to those of skill in the art.

EXAMPLES

The following Examples are intended to further illustrate the invention and are not intended to limit the scope of the invention in any matter whatsoever. In such Examples, all proportions expressed are by weight unless otherwise specified.

Example 1

3000 grams of anhydrous sorbitol melt (containing approximately 0.2% water by weight), obtained from a molten feed tank, were placed into a stainless steel beaker standing on a hot plate at a temperature at 200° F. (93° C.).

In a separate beaker, 1.5 grams of Red 40 dye was added to 50 ml. of Benadryl Exlair. The dye was completely mixed into the Exlair using a propellor mixer.

When the dye was throughly dispersed into the Exlair, the Exlair/dye dispersion was mixed thoroughly into the molten sorbitol at 200° F. This was done using a propeller mixer, creating a vortex to which the colored Exlair was added and mixed.

Once the molten sorbitol was a uniform color (as determined by drawing a sample from it and checking for color uniformly) the colored sorbitol melt containing the Benadryl Exlair was transferred to a jacketed Readco Sigma Blade mixer fitted with a heating jacket in order to maintain the temperature at 195° F. (91° C.) to avoid supercooling the melt when such melt was transferred into the mixer. The melt was agitated at Speed 4 on the speed dial of the mixer and the melt was maintained at 195 degrees through crystallization. Upon crystallizing the melt was observed to be a dry hard mass with a uniform color. The uniform color of the final crystalline mass is indicative of the Benadryl Exlair being uniformly dispersed throughout the sorbitol on crystallizing, and of the finding that no separation occurred.

The crystalline sorbitol/Benadryl Exlair cocrystallized mass was removed from the Readco and ground to a −20/+60 mesh fraction. The powder so produced was observed to be of uniform color indicating that no separation of the Benadryl Exlair was observed to have occurred during the grinding step. Moreover, after several weeks the powder retained its uniform color indicating that no "leaching out" of the ground powder had occurred.

495 grams of the −20/+60 cocrystallized sorbitol/Benadryl Exlair were mixed with 5 grams of magnesium stearate and this mixture was run on a Stokes B-2 press using ⅜ inch flat faced beveled edge punches to mak a 1.0 gram tablet using 3.0 tons pressure. The resulting tablets had a uniform color and no active was noted on the surface of the tablet or on any of the surfaces of the granulation (sorbitol/magnesium stearate) from which the tablet was made.

EXAMPLE 2

Molten sorbitol containing about 10 percent by weight mannitol and 10 percent by weight dimethylisosorbide (DMI) and 0.2 percent by weight moisture was fed at a temperature of 95° C. continuously into a Readco Continous Mixer similar to that described in U.S. Pat. No. 3,618,902 having 24 inch diameter dual mixing blades. The mixer was operator under continuous steady state conditions with an output rate ranging from 1950-2025 lbs. per hour. The cooling jacket temperature was regulated between a temperature of 22° C. and 25° C. with a shaft rotation speed of 10.5 r.p.m. such that the effluent nozzle water temperature varied from 86° to 88° C. The crystalline paste discharged under such condition ranged from 80-92 percent by weight crystalline material. The crystalline paste discharge was then passed through a spinerette having cylindrical openings of 12 millimeters in diameter. The extrudate was collected on moving belt in an atmosphere of cool air and after cooling for one minute, was cut into two inch lengths and thereafter placed on closed storage trays and permitted to stand at room temperature for a period of three days. The material was ground to a particular size of −20/+60 mesh U.S. sieve series average particle size of 300 microns. Scanning electron micrographic examination at 2000× magnification showed individual crystals having widths of about 1 micron in diameter mixed with glass and included DMI.

EXAMPLE 3

90 parts silica gel (Syloid ® silica) was mixed with 10 parts dimethylisosorbide (DMI) and thereafter mixed with molten sorbitol in a stirred, covered heated feed tank to provide a molten sorbitol containing 20 percent silica and 2.5 percent dimethylisosorbide. This material was then fed into 24 inch diameter dual mixing device under conditions described in Example 2. The product was ground to −20/+60 mesh (U.S. sieve series) to produce a powder having a liquid pharmaceutically active compound included therein. No separation or leaching out of such liquid active was observed.

EXAMPLE 4

Into a water heated (90° C.) sigma blade Day Mixer were placed 3,960 grams of molten sorbitol (130° C.) and 40 grams of dimethylisosorbide. This material was mixed until uniform and thereafter 10 grams of sorbitol crystals were added as seed material while the sorbitol/dimethylisosorbate blend was maintained in a molten state. This material was mized until crystals began to form in the molten mass. The crystallizing mass was then removed from the mixer and placed on pans and thereafter stored at 21° C. at 48 percent relative humidity for 24 hours to allow the mixture to thoroughly crystalline. After 24 hours, this material was broken up and placed in 1 quarts laboratory Waring Blender to obtain a fine particle distribution of crystalline sorbitol having included dimethylisosorbide (1 percent by weight).

The ground material, when placed in an open container, remained stable and did not undergo excessive caking thereby indicating that of the dimethylisosorbide remained in the sorbitol crystals and did not leak from the fractured material.

What is claimed is:

1. A pharmaceutical composition comprising crystalline sugar alcohol selected from the group consisting of sorbitol, mannitol, co-crystallized sorbitol with mannitol, xylitol, maltitol, lactitol, cellobiitol and hydrogenated starch hydrolysates having at least one liquid pharmaceutically active compound uniformly dispersed within its crystal matrix.

2. A composition in accordance with claim 1 wherein said sugar alcohol is sorbitol.

3. A composition in accordance with claim 1 wherein said sugar alcohol is co-crystallized sorbitol and mannitol.

4. A composition in accordance with claim 3 wherein said sorbitol contains between about 5 and about 15 percent by weight mannitol.

5. A composition in accordance with claim 1 wherein said liquid pharmaceutically active compound is a compound which is normally a solid at ambient conditions but which is in solution form.

6. A composition in accordance with claim 1 wherein said composition is in the form of a tablet.

7. A composition in accordance with claim 1 wherein said composition is in the form of chewing gum.

8. A composition in accordance with claim 1 wherein said composition is in the form of tooth-paste.

* * * * *